United States Patent [19]

Daniel

[11] 4,123,427

[45] Oct. 31, 1978

[54] METHOD FOR THE PURIFICATION OF MYCOBACTERIAL PROTEIN ANTIGENS AND RESULTING PRODUCT

[76] Inventor: Thomas M. Daniel, 3028 Chadbourne Rd., Shaker Heights, Ohio 44120

[21] Appl. No.: 708,950

[22] Filed: Jul. 27, 1976

[51] Int. Cl.² .............................................. A23J 1/06
[52] U.S. Cl. ............................ 260/112 B; 260/112 R; 424/88; 424/92
[58] Field of Search ...................... 260/112 R, 112 B; 424/88

[56] References Cited

U.S. PATENT DOCUMENTS

| | | | |
|---|---|---|---|
| 3,639,559 | 2/1972 | Tax .................................. | 424/88 X |
| 3,875,002 | 4/1975 | Landi et al. .................. | 260/112 R X |
| 3,879,369 | 4/1975 | Nolan ............................... | 260/112 R |
| 4,020,268 | 4/1977 | Nishikawa et al. .......... | 260/112 R X |

OTHER PUBLICATIONS

Daniel et al., *Am. Review Resp. Disease*, vol. 112 (1975), pp. 639–644.
Janicki et al., *Am. Review Resp. Disease*, vol. 104 (1971), pp. 602–604.
Daniel, *Am. Review Resp. Disease*, vol. 113 (1976), pp. 717–719.
Rothen et al., *Helvetica Chimica Acta*, vol. 54, Fasc. 4 (1971), pp. 1208–1217.
Laguerre et al., *Chemical Abstracts*, vol. 84:103,712x (1976).
Kuwabara, *Chemical Abstracts*, vol. 82:167,218g (1975).

*Primary Examiner*—Walter C. Danison
*Attorney, Agent, or Firm*—Fay & Sharpe

[57] ABSTRACT

The subject invention is directed in general to a method of preparing an antigen using immunoabsorbent affinity chromotography particularly in cases where an antigen is used for the recognition and measurement of hypersensitivity and where antigenic specificity is desired as, for example, in hypersensitivity to tuberculin, histoplasmin, coccidioidin, and common inhalant allergens. More particularly, this invention consists of a method which includes the following steps: immunizing a suitable host animal, usually a goat, with a preparation containing the desired antigen, collecting antisera from the animal and selecting the most specific antisera; isolating the antibody containing gamma globulin from the selected antiserum; coupling the globulin to an inert substrate (usually agarose beads) by chemical bonding with cyanogen bromide to form an absorbent in which the antibody acts as ligand; using the absorbent to bind selectively the desired antigen in a crude mixture containing the antigen; eluting the antigen from the absorbent by breaking the antigen-antibody bond with urea, usually at 4 – 6 molar (also referred to as M in the specification) and about pH 7 – 9; and then recovering the eluted antigen and preparing it in a form suitable for its intended use. By this method a highly purified, improved tuberculin skin test reactant is produced from culture filtrate which is prepared by growing tubercle bacilli in a liquid, synthetic medium, collecting and sterilizing by filtration the liquid phase of this culture (alternatively a soluble extract of the bacillary mass may be used), and then processing this filtrate and purifying the antigen by the steps described.

26 Claims, 5 Drawing Figures

METHOD FOR THE PURIFICATION OF MYCOBACTERIAL PROTEIN ANTIGENS AND RESULTING PRODUCT

BACKGROUND OF THE INVENTION

Field of the Invention

Crude extracts of mycobacteria contain many antigens of varying chemical composition. Some of these antigens are probably species specific; others are known to be shared among many species and almost certainly contribute to the antigenic cross reactivity commonly observed with mycobacterial extracts. Fractionation of either mycobacterial culture filtrates or of mycobacterial cell extracts has been employed by many investigators in search of isolated, purified antigens.

Identification and Nomenclature of Mycobacterial Antigens

Despite decades of effort in this field, it was not until the work of Janicki and his collaborators from several independent American laboratories in 1971 that a widely and readily applied system of identification and nomenclature for mycobacterial antigens became available. [Janicki, B. W., Chaparas, S. D., Daniel, T. M., Kubica, G. P., Wright, G. L., Jr., and Yee, G. S.: A reference system for antigens of Mycobacterium tuberculosis. Amer Rev Respir Dis, 104:602–604, 1971.] Janicki and his coworkers prepared an unheated reference culture filtrate antigen from Mycobacterium tuberculosis, $H_{37}Rv$ and an homologous polyvalent goat antiserum suitable for use in immunoelectrophoresis.

The immunoelectrophoresis reference reagents and nomenclature, sometimes designated as United States-Japan reagents because they were produced under the sponsorship of the United States-Japan Cooperative Medical Sciences Program, have been used by a number of investigators to identify their products or to relate their methodologies to a common reference point. Unless otherwise stated Arabic numeral designation of antigens always refers to the nomenclature of Janicki and collaborators as in the reference noted above.

Early Investigations

Robert Koch first reported the production of a product which he named Old Tuberculin (OT) in 1890. Tuberculin skin testing using this material was rapidly accepted into clinical and epidemiologic practice in both veterinary and human medicine. However, nonspecific reactions to OT were soon encountered, and it was recognized that this nonspecificity probably resulted from environmental contact with other, often nonpathogenic, species of mycobacteria which shared cross reactive antigens with virulent mammalian tubercle bacilli. These early events have been elegantly reviewed by Edwards and Edwards. [Edwards, P. Q., and Edwards, L. E.: The story of the tuberculin test from an epidemiologic viewpoint. Amer Rev Resp Dis, 81 (suppl): 1–45, 1960.]

In 1932 Florence Seibert first attempted to recover purified tuberculoprotein from OT using trichloracetic acid precipitation [Seibert, F. B., and Munday, B.: The chemical composition of the active principle of tuberculin. XV. A precipitated purified tuberculin protein suitable for the preparation of a standard tuberculin. Amer Rev Tuberc, 25:724–737, 1932.], and in 1934 she described the preparation of a material termed Tuberculin Purified Protein Derivative (PPD) prepared from Old Tuberculin by repeated precipitation with ammonium sulfate at 50 percent saturation and neutral pH. [Seibert, F. B.: The isolation and properties of the purified protein derivative of tuberculin. Amer Rev Tuberc, 30: 713–720, 1934.] As in the manner of Robert Koch, the OT was derived from eight-week-old pellicle cultures on synthetic medium of M. tuberculosis. The cultures were steamed or autoclaved prior to filtration, a procedure which undoubtedly led to considerable protein loss from heat denaturation. PPD rapidly became and remains the standard preparation for clinical tuberculin skin testing. OT also remains in use for this purpose, especially in the form of disposable multiple puncture test units and veterinary products. Affronti prepared PPDs from other species of mycobacteria [Affronti, L. F.: Purified protein derivatives (PPD) and other antigens prepared from atypical acid-fast bacilli and Nocardia asteroides. Amer Rev Tuberc, 79:284–295, 1959.], and these have been used in epidemiologic and clinical studies of turberculin cross reactivity.

The first major attempt to purify isolated antigens from mycobacteria by chemical fractionation was also made by Florence Seibert using precipitation with alcohol and acetic acid. For here studies Seibert used eight-week-old pellicle cultures of M. tuberculosis grown on synthetic medium. Filtrates were prepared from these cultures without heating, thus sparing the heat denaturation incurred in the classic preparation of OT and PPD, and most workers since have followed her lead and used unheated starting materials in their attempts to purify mycobacterial antigens. Seibert obtained three major proteins and two polysaccharides, each distinct in physicochemical properties which she designated proteins A, B, and C and polysaccharides I and II. The proteins were characterized by increasing electrophoretic mobility at ph 7.7.

Protein A was precipitable with 70 percent ethanol at pH 4.6. It was capable of eliciting tuberculin skin tests in man and was more potent than equal weights of PPD. It was recognized by Seibert that protein A contained at least two components, one of which was thought to be a protein with a molecular weight of 35,000 to 42,000. Studies by Daniel and Affronti demonstrated that protein A contained antigens 1, 2, 5, and 6 and probably also 4. [Daniel, T. M., and Affronti, L. F.: Immunoelectrophoretic analysis of antigenic constituents of Seibert fractions of mycobacterial culture filtrates. Identification with the proposed United States-Japan reference nomenclature. Amer Rev Respir Dis, 108:1244–1248, 1973.] Protein B was precipitable with 30 percent ethanol at pH 4.6. It was also capable of eliciting tuberculin skin tests in man and was also more potent than PPD. It was found to have a sedimentation constant of 2.0 S and a molecular weight of approximately 20,000 daltons. Immunoelectrophoretic studies by Daniel and Affronti showed protein B to contain antigens 1, 2, 5, 6, and 7. It was distinct from protein A in this study chiefly by virtue of containing much less antigen 6 and significant quantities of antigen 7. Rapidly migrating protein C was insoluble in acetic acid at pH 4.0, and some preparations of this protein were thought to be contaminated with nucleoprotein. It was relatively inactive as a skin test antigen. By immunoelectrophoresis it contained considerably less antigenic material than the other two proteins, with antigens 2, 6, and 7 being recognized and two unidentified anodal antigens also found.

RECENT PHYSICOCHEMICAL FRACTIONATION STUDIES

During the past two decades methods of physicochemical fractionation which carry relatively little risk of denaturation have become available and have been used in attempts to isolate mycobacterial antigens. The methods employed have included ion exchange chromatography, gel filtration chromatography, isoelectric focusing, and zonal electrophoresis with or without the molecular sieving effect of an acrylamide gel supporting system. Salt or solvent solubility has often been used in combination with these techniques.

Ion exchange chromatography with diethylaminoethyl (DEAE) cellulose was used as a sole fractionation procedure by Kniker and LaBorde. [Kniker, W. T., and LaBorde, J. B.: The separation of mycobacterial antigens by ion-exchange chromatography. I. Details of chromatographic and immunologic procedures and results with four strains of M. tuberculosis. Amer Rev Respir Dis, 89:29-40, 1964.] Stepwise increases in ionic strength with decreasing pH led to the elution of several antigen-containing peaks when culture filtrates of M. tuberculosis were chromatographed. The chromatograms revealed excellent resolution, but serologic analysis demonstrated that many antigens were present in more than one chromatographic peak. Using heterologous rabbit antisera many of the purified antigen-containing peaks were found to be cross reactive with other mycobacterial species. Subsequently Kniker used the same methods to study Seibert proteins A, B, and C. Each was found to have a predominant component which could be associated with one of the peaks observed when whole culture filtrate was chromatographed. However, each was also found to contain multiple antigens. Kniker also chromatographed filtrates from three other mycobacterial species, again obtaining good chromatographic resolution and observing a multiplicity of antigens, both specific and cross reactive.

None of the ion exchange chromatographic studies led to the recovery of fractions containing single antigens, although in every case some degree of purification was achieved. Gel filtration chromatography with high porosity G-100 and G-200 Sephadex was compared with DEAE cellulose chromatography by Castelnuovo. [Castelnuovo, G., Yamanaka, S., Zoppis, M., and Dotti, E.: The protein components of Mycobacterium phlei: Fractionation procedures. Tubercle, 50:194-202, 1969.] The chromatograms did not show good resolution, but it was felt that better results were obtained with Sephadex than with DEAE cellulose. Moderate resolution was reported by Lind [Lind, A.: Immunologic analysis of mycobacterial fractions. Amer Rev Respir Dis, 92 (suppl):54-62, 1965] when Sephadex G-100 was used to fractionate a concentrated filtrate of M. avium, but no single antigen fractions were recovered. Low porosity Sephadex G-25 and G-50 were used by Baer and Chaparas to fractionate the acid soluble and insoluble, nondialyzable components of culture filtrates of M. bovis, BCG strain. [Chaparas, S. D., and Baer, H.: The immunology and chemistry of tuberculin. II. Chromatography with Sephadex of the nondialyzable tuberculin-active constituents of BCG culture filtrate. Amer Rev Respir Dis, 89:41-48, 1964.; Tuberculin reactivity of a carbohydrate component of unheated BCG culture filtrate. Science, 146:245-247, 1964; Baer, H.: Tuberculin reactivity and other immunochemical and physical properties of fractions derived from BCG culture filtrate. Amer Rev Respir Dis, 92 (suppl):42-48, 1965; Chaparas, S. D., Baer, H., and Godfrey, H.: In vivo and in vitro studies on tuberculin active polysaccharide and protein fractions. Zeit Immunit Allerg Immunol, 137:134-143, 1969; and Chaparas, S. D., Thor, D. E., Godfrey, H. P., Baer, H., and Hedrick, S. F.: Tuberculin-active carbohydrate that induces inhibition of macrophage migration but not lymphocyte transformation. Science, 170:637-639, 1970.] The acid insoluble material was resolved by this procedure into two pools, both high in protein content, both containing multiple antigenic constituents when studied with appropriate antisera, and both capable of eliciting delayed skin test reactions in homologously and heterologously sensitized guinea pigs. The acid soluble material was resolved into three fractions. The first eluted was largely polysaccharide. It elicited delayed skin test reactions and inhibited macrophage migration in sensitized animals. These properties could not be eliminated by treatment with pronase and trypsin. This material did not stimulate mitogenesis in cultured lymphocytes. This dichotomy between skin test reactivity and lymphocyte mitogenicity was also observed with the polysaccharide preparation studied by Daniel and Hinz. [Daniel, T. M., and Hinz, C. F., Jr.: Reactivity of purified proteins and polysaccharides from Mycobacterium tuberculosis in delayed skin test and cultured lymphocyte mitogenesis assays. Infect Immun, 9:44-47, 1974.] The remaining two fractions were approximately 50 percent polysaccharide. They also elicited tuberculin skin test reactions, and their antigenicity was reduced by enzyme treatment. All three fractions contained multiple antigens when assayed serologically.

Janicki and his collaborators used zonal electrophoresis to fractionate culture filtrates of M. tuberculosis, [Janicki, B. W., Aron, S. A., Schechter, G. P., and McFarland, W.: Tuberculin antigens active in human lymphocyte blastogenesis. Proc Soc Exptl Biol Med, 141:809-813, 1972.] A continuous flow paper curtain technique was used, and reference antiserum was used to identify the antigens in the eluted fractions. A polysaccharide-rich anodal pool of fractions contained antigens 1, 2, and 3. Cathodal pools were largely proteinaceous. Janicki concluded that as a single technique zonal electrophoresis was unlikely to yield isolated antigenic constituents with the possible exception of polysaccharides. It was subsequently shown that the polysaccharide pool evoked little response in cultured lymphocytes from tuberculin positive donors, whereas the most cathodal protein pool did serve as an antigenic mitogen for cultured lymphocytes.

Affinity Chromatography

Affinity chromatography is a purification method based on highly specific, dissociable interactions between two macromolecules. It is among the most versatile and powerful purification methods available in the field of immunochemistry. One of the interacting macromolecules is complexed to an inert substrate, frequently agarose, to prepare an absorbent. Crude material containing the other reactant for which purification is sought is mixed with the absorbent under conditions which will allow the two substances to complex with one another. Conditions favoring reaction are maintained while all contaminating substances are washed from the absorbent. Conditions are then changed to those which favor dissociation, and the absorbed reactant is eluted. This subject has been comprehensively reviewed by Cuatrecasas and Anfinsen. [Cuatrecasas, P., and Anfinsen, C. B.: Affinity chromatography. Ann Rev Biochem, 40:259-278, 1971.]

Antigenic Specificity

From the material presented in this review it is possible to make a number of broad inferences concerning the specificity of mycobacterial antigens. It is quite clear that all unpurified mycobacterial extracts contain multiple antigens. Polysaccharide antigens, consisting principally of arabinogalactan and arabinomannan, are present in large quantities in most of these, including Old Tuberculin, and are difficult to remove completely by physicochemical means. Both chemically and immunologically these polysaccharides have been demonstrated to be present in many species of mycobacteria and in nocardia and corynebacteria as well. Their potential antigenicity seems well established, with the possible exception of mitogenicity in in vitro lymphocyte cultures. It is likely that these polysaccharides contribute significantly to the nonspecificity so often observed with mycobacterial extracts.

In contrast, it is likely that some, although most certainly not all, mycobacterial proteins are species specific antigens. The ion exchange chromatographic studies of Kniker and of Diena and coworkers [Diena, B. B., Yugi, H., Wallace, R., Carriere, J., and Greenberg, L.: The bentonite flocculation test in the serology of tuberculosis. I. Purification of BCG antigens. Canad J Microbiol, 14:881-885, 1968] support this hypothesis. Similar conclusions can be drawn from studies using polyacrylamide gel electrophoresis, especially that of Minden and Farr. [Minden, P., and Farr, R. S.: Binding between components of the tubercle bacillus and humoral antibodies. J Exptl Med, 130:931-954, 1969.] The recent collaborative study of Janicki and several collaborators has demonstrated skin test specificity in homologously and heterologously sensitized guinea pigs and found this specificity to be associated with acrylamide gel electrophoresis fractions containing principally antigens 5 and 6. [Janicki, B. W., Wright, G. L., Jr., Daniel, T. M., Chaparas, S. D., Good, R. C., and Goldstein, R. A.: Isolation and characterization of M. tuberculosis culture filtrate antigens. To be published.]

Relatively little is known concerning antigen 5; no isolation nor characterization of this antigen has been published. Preliminary work by this inventor suggests that it is a glycoprotein. It binds loosely to concanavalin A, suggesting that the carbohydrate moiety contains mannose or glucose. It reacts poorly in the Lowry protein reaction [Lowry, O. H., Rosebrough, N. J., Farr, A. L., and Randall, R. J.: Protein measurement with the Folin phenol reagent. J Biol Chem 193: 265-275, 1951], suggesting that it has relatively little tyrosine. When electrophoresed in 7.0 percent acrylamide gel at pH 9.5 it has an Rf of 0.61. This mobility is not similar to the specific antigen described by Minden and Farr [J Exptl Med, 130:931-954, 1969]. To date this inventor has been able to demonstrate this antigen in culture filtrates from M. tuberculosis, M. kansasii, M. xenopi, and no other organism.

Antigen 6 is present in many mycobacteria. It has been shown to share an antigenic determinant when prepared from M. tuberculosis with a major antigen of M. szulgai, and also to contain a separate, nonshared antigenic determinant [Daniel, T. M. and DeMuth, R. W.: Immunological Chemical Analyses of a Major Antigen of Mycobacterium szulgai. Journal of Infectious Disease, Vol. 135, p. 778-786]. Subsequent unpublished observations by this inventor have demonstrated similar occurrences of shared and specific antigenic determinants on the antigen 6 molecule of several species of mycobacteria. As purified by Daniel and Ferguson [Daniel, T. M. and Ferguson, L. E.: Purification and characterization of two proteins from culture filtrates of Mycobacterium tuberculosis $H_{37}$ Ra strain. Infect Immun 1: 164-168, 1970] and designated by them as protein $a_2$ antigen 6 is a protein with a molecular weight of 45,000 to 48,000. The alpha antigen of Yoneda and Fukui [Yoneda, M. and Fukui, Y.: Isolation, purification, and characterization of extracellular antigens of Mycobacterium tuberculosis. Am Rev Respir Dis 92 (suppl): 9-18, 1965] is probably the same antigen. They have demonstrated antigenic specificity and shared determinants for their alpha antigen in a similar fashion [Yoneda, M., Fukui, Y., and Yamanouchi, T.: Biken J 8: 201-223, 1965].

The beta antigen of Yoneda and Fukui is perhaps the best characterized and studied antigen with apparent species specificity, but it is not possible to relate this antigen to other described proteins. [Yoneda, M., Fukui, Y., and Yamanouchi, T.: Extracellular proteins of tubercle bacilli. V. Distribution of alpha and beta antigens in various mycobacteria. Biken J, 8:201-223, 1965].

From the foregoing, it is quite clear that research on the purification of mycobacterial antigens has not yet reached the goal of producing specific and readily standardizable antigens. Therefore, the need for purified and well standardized antigens is great. Not only are they necessary for accurate clinical diagnosis of tuberculous infection, but also mycobacterial antigens serve as standards in the assessment of cell-mediated (T lymphocyte) immunologic functions in a host of clinical and fundamental biological situations.

SUMMARY OF THE INVENTION

The tuberculin test is used in clinical immunologic studies, both in man and in animals, and consists of the injection of an extract of tubercle bacilli into the host with the expectation that an infected individual will display a reaction not otherwise noted in an uninfected individual. However, in the past false positive reactions have frequently occurred. The cause of false positive reactions has been reasonably well identified as hypersensitivity to other organisms related to tubercle bacilli. Within the genus Mycobacterium (a genus which includes the tubercle bacillus and related organisms) there has been noted a variety of saprophytic or uncommonly pathogenic species, including organisms which live in soil or in ordinary tap water. Two basic approaches have been taken in an effort to avoid false positive reaction problems. One has been to recognize that reaction sizes, both specific and nonspecific, have normal or Gaussian distributions with the mean of specific reactions generally larger than the mean of non-specific reactions. In practice it has been found empirically that reactions larger than one standard deviation below the mean specific reaction size are usually larger than one standard deviation above the mean of the nonspecific reaction sizes. This allows separation of reactions into specific and nonspecific simply on the basis of size with moderate confidence. However, small reactions must always be classified as "doubtful".

The other approach has been to make better antigens, i.e. more specific extracts to inject. This approach has been in use since the 1930s. A variety of efforts have been made in this direction, but nearly all the extracts produced have contained multiple antigens, some specific for the tubercle bacillus and others widely distributed among mycobacteria. Currently there are two tuberculin skin test materials in use. One is a crude preparation of culture filtrate termed Old Tuberculin (OT) which has the advantage of being extremely stable and not requiring refrigeration for storage. It is commonly used on disposable multiple puncture devices which offer increased user convenience. The other tuberculin product is a more specific material requiring refrigeration, having a relatively short shelf life, and usually administered intradermally by syringe and needle. It was made during 1934 by Florence Seibert with the designation PPD (purified protein derivative). PPD is, in fact, not very pure but makes a better extract than Old Tuberculin (OT), a much cruder material. PPD is known to produce fewer false positives. From 1934 to the present others have attempted to make a better material as described in some detail by Edwards et al in "The Story of the Tuberculin Test from an Epidemiologic Viewpoint" [Amer Rev Respir Dis, 81 (suppl):1–45, 1960].

This application is important, in that a monospecific antigen is obtained using affinity chromatography. In the study of biology, it is known that many molecules interact with each other, an example of which is the reaction of an enzyme with a substrate. Pepsin is an enzyme in the stomach, and it reacts with protein to break down the protein. In the reaction process, the first thing the enzyme does is bind to protein molecule. If one desires to purify pepsin, by way of an example, a substrate protein molecule is fixed to a carrier to make it stable and inert, and for such a purpose beads of agar gel may be used. The pepsin molecule has a specific binding site which is shaped to fit and attach to its substrate. Crude stomach juice is put through the chromatography column, and the pepsin molecule attaches to the substrate absorbent. Following this, the enzyme-substrate bond is dissociated to yield the enzyme in pure form. This, of course, is a basic procedure which has been used extensively and known in the prior art literature. One molecule which may be attached to the beads of agar gel is an antibody molecule. Antibody molecules of the common variety have two specific binding sites, and these binding sites are very specific for individual antigens, not just whole classes but individual antigens. It is possible to use cyanogen bromide, a chemical reagent, to complex these antibodies to an inert carrier such as agarose. However, the exact chemistry of that particular bond is not well understood. The antibody is then used as a ligand for complexing a specific antigen to the absorbent.

In prior patented art and literature, there are only a few instances of a specific antibody being attached to a substrate. Once an antibody attaches to a specific antigen, the bond is extremely tight and therefore very difficult to break, not lending itself to standard chromatography techniques. In the purification of a crude extract of tubercle bacilli, this bond must be dissociated without disrupting the absorbent so that gamma globulin is not introduced into the product since it is a foreign protein. If such a contaminated extract were administered to an individual, he might develop hypersensitivity to it. Other prior users have applied the principle of breaking an antigen bond under acid conditions, dropping the pH below pH 3 and sometimes raising the salt content as well. Antigens of tubercle bacilli cannot withstand this because aspartic acid and asparagine peptide bonds important to the integrity of major mycobacterial antigens break at that pH.

The method of this invention consists of immunizing a suitable host animal (usually a goat, although it is possible to use other animal species, for example, rabbits, sheep and/or horses) with a preparation containing the desired antigen and then collecting antisera from the animal and selecting the most specific antisera. Other steps of this invention include isolating an antibody containing gamma globulin and coupling it to an inert substrate (generally agarose beads) by a chemical bond with cyanogen bromide to form an absorbent in which the antibody acts as ligand, and eluting the antigen from the agarose beads to break the antigen-antibody bond with urea from 4–6 M and pH 7–9, and then recovering the purified antigen and preparing it in a suitable form.

DETAILED DESCRIPTION OF THE INVENTION

Turberculin antigens, derived from culture filtrates of mycobacteria, are widely used in the clinical and laboratory study of cellular hypersensitivity. All currently available tuberculin antigen preparations are complex mixtures, containing both species-specific and nonspecific antigens. There have been many attempts to improve the specificity of culture filtrate-derived mycobacterial antigen preparations by physicochemical fractionation of culture filtrate (CF) materials. To date this approach has met with very limited success.

In this invention immunoabsorbent affinity chromatography is employed for the purification of mycobacterial antigens. Towards this goal conditions for the preparation and use of such immunoabsorbents were studied systematically. After preliminary experiments in which sodium iodide, 2,4-diaminobutane, and urea were compared as eluants, urea was selected as an agent to dissociate antigen-antibody bonds and permit elution of the absorbed antigen; and the effect of urea concentration on the elution process, the antigen, and the absorbent, was studied.

EXAMPLE I

Culture filtrates of Mycobacterium tuberculosis, $H_{37}Ra$ grown on totally synthetic medium were prepared as previously described. [Daniel, T. M., and Ferguson, L. E., 1970: The purification and characterization of two proteins from culture filtrates of Mycobacterium tuberculosis, $H_{37}Ra$ strain. Infec Immun 1:164-168.] Prior to use these filtrates were dialyzed against 0.15 M sodium chloride buffered with ten percent of 0.15 M sodium phosphate buffer at pH 7.2 (PBS). When desired, trace amounts of radioactive culture filtrate were added. Labelled culture filtrate was prepared by iodinating dialyzed culture filtrate with $^{125}I$ by the method of Greenwood and Hunter. [Greenwood, F. C., and Hunter, W. M., 1963: The preparation of $^{131}I$-labelled human growth hormone of high specific radioactivity. Biochem J 89:114-123.] Radioautography of immunoelectrophoresis of the isotopically labeled culture filtrate demonstrated labeling of all of the major identifiable antigenic constituents.

Goat antisera were prepared in animals immunized as previously taught [Daniel, T. M., Good, R. C., and Janicki, B. W., 1975: Immunoelectrophoresis of Mycobacterium tuberculosis antigens. Comparative analysis of cell extract and culture filtrate antigens. Am Rev Respir Dis, 112:639-644] with soluble mycobacterial antigens emulsified with complete Freund's adjuvants and subsequently boosted with soluble antigen. These antisera were all polyvalent. Other antisera were prepared by the repeated injection of animals with physicochemically purified mycobacterial antigens without using Freund's adjuvants. The most specific antisera produced by these animals were selected for the preparation of monospecific immunoabsorbents. Goat gamma globulin (GGG) was prepared from whole goat serum by precipitation with ammonium sulfate at 33 percent saturation at 4° C. When desired, trace amounts of GGG similarly prepared, labeled with radioactive $^{125}I$ by coupling with chloramine-T and purified of free iodine on Sephadex G-75, were added to the GGG.

Agarose beads in gel form (Sepharose 4B, Pharmacia Fine Chemicals, Piscataway, N.J.) were used to prepare immunoabsorbents using a method based upon that of Bing. [Bing, D. H., 1971: Purification of the first component of human complement by affinity chromatography on human gamma globulin linked to sepharose. J Immunol 107:1243-1249.] Agarose was washed repeatedly on a Buchner funnel with large volumes of distilled water, reconstituted to approximately the original thickness with water, and then suspended in an equal volume of water. Working in a fume hood, a similar volume of 10 percent cyanogen bromide was added. With constant stirring, the mixture was adjusted to pH 10 or other desired pH with 4 N sodium hydroxide and incubated for 15 to 30 minutes at room temperature. The agarose was then promptly washed with large volumes of cold 0.1 M sodium bicarbonate at pH 9 on a Buchner funnel and resuspended as a slurry of approximately 10 percent in 0.1 M sodium bicarbonate. GGG, sometimes containing radioactive tracer, was dialyzed against 0.1 M sodium bicarbonate buffer pH 9 to which sodium chloride had been added to 0.5 M concentration. It was then added in a known quantity to 5 ml of the activated agarose. This slurry was incubated for 16 hours or other desired time with constant gentle stirring at 4° C. The agarose was then washed on a Buchner funnel with large volumes of 0.1 M sodium borate buffer at pH 9 alternating with 0.1 sodium acetate at pH 5. The agarose-GGG immunoabsorbent thus prepared was finally suspended in PBS.

The immunoabsorbent slurry was poured into a 1.0 cm glass chromatography column, and equilibrated in the column with PBS. Three preliminary sham elutions of the column were then performed, the column being washed with PBS after each. Culture filtrate was then added to the column and washed in slowly. The column was then washed exhaustively with PBS and elution finally carried out with 50 ml of the desired eluant using a drop counting fraction collector. Absorbent columns were washed promptly with PBS after each elution. When stored overnight or longer between elutions, they were left filled with PBS to which 0.1 percent sodium azide was added and placed in a cold room at 4° C.

Radioactivity was estimated by counting in a well type gamma counter. Column elutions were monitored by determining optical absorption of individual fractions at 280 mu. Immunoelectrophoresis was carried out as previously described for mycobacterial antigens. [Janicki, B. W., Chaparas, S. D., Daniel, T. M., Kubica, G. P., Wright, G. L., and Yee, G. S., 1971: A reference system for antigens of Mycobacterium tuberculosis. Am Rev Respir Dis, 104:602-604.] Two-dimensional immunodiffusion in agar gel was carried out in agar gel layered on standard microscope slides. One percent agar (Special Agar-Noble, Difco Laboratories, Detroit, Mich.) was made up in barbital-glycine buffer containing sodium barbital 8.62 g and glycine 22.46 g per liter with 0.1 percent sodium azide added. Three ml of agar were layered on a microscope slide and 3.0 mm diameter wells cut in the agar in the desired patterns with 8.0 mm distances between well centers. Eluted fractions were lyophilized to dryness, reconstituted in small volumes, and restudied before being considered negative by immunodiffusion or immunoelectrophoresis. Skin testing was carried out as previously described [Daniel, T. M., 1975: The antigenicity in guinea pigs and monkeys of three mycobacterial polysaccharides purified by affinity chromatography with concanavalin A. Am Rev Respir Dis, 111:787-793] using groups of six guinea pigs sensitized by the subcutaneous injection in a posterior nuchal site of 10 mg (dry weight) of unheated M. tuberculosis, H₃₇Ra cells which were washed free of culture medium, suspended in one percent phenol overnight, and then suspended in incomplete Freund's adjuvant (Difco Laboratories, Detroit, Mich.). Chemical estimations of protein content were performed by the method of Lowry and coworkers. [Lowry, O. H., Rosebrough, N. J., Farr, A. L., and Randall, R. J., 1951: Protein measurement with the Folin phenol reagent. J Biol Chem 193:265–275.] The procedure described in Example I is referred to as the standard conditions. Using the method as described in this Example 1 and using an immunoabsorbent prepared from an antiserum selected for its specificity for antigen 5, antigen 5 of high purity can be prepared.

EXAMPLE II

Figure 1:
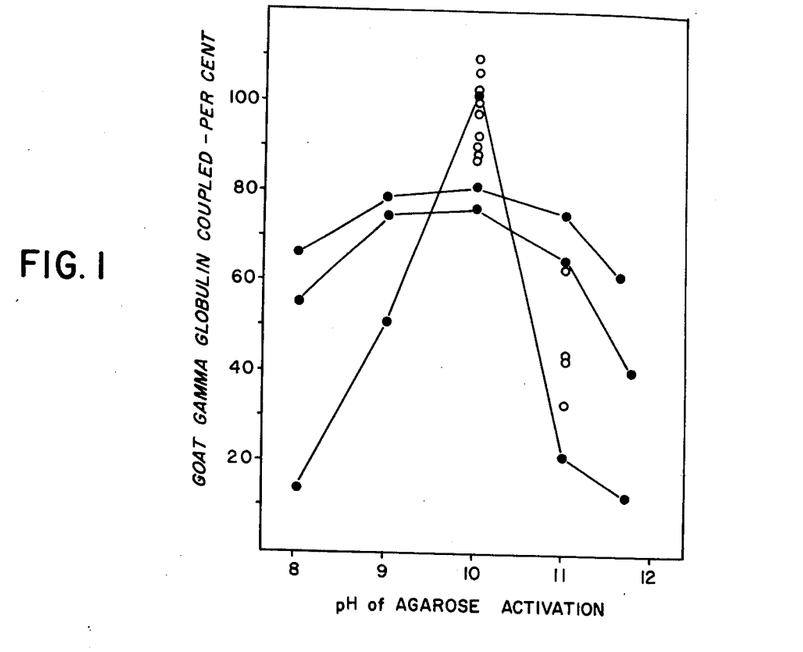
FIG. 1 shows the effect of pH of cyanogen bromide activation of agarose upon the subsequent coupling of goat gamma globulin (GGG) to the agarose. The percent of the total available GGG bound to the agarose is plotted over the pH range 8.0 to 11.7. Three experiments are shown separately in which the entire pH range was studied. Single experiments at pH 11.0 and one at 10.0 are also shown and are indicated by open circles (o).

The effect of pH on agarose activation. Three experiments were carried out in which the pH of agagrose activation by cyanogen bromide was varied systematically and related to the subsequent coupling of GGG under standard conditions. In FIG. 1 the percent coupling achieved is shown for each of these experiments. Also shown are single experiments with activation at pH 11.0 or pH 10.0. pH 10.0 appeared to provide both the maximum and the most reproducible degree of protein coupling.

Figure 2:
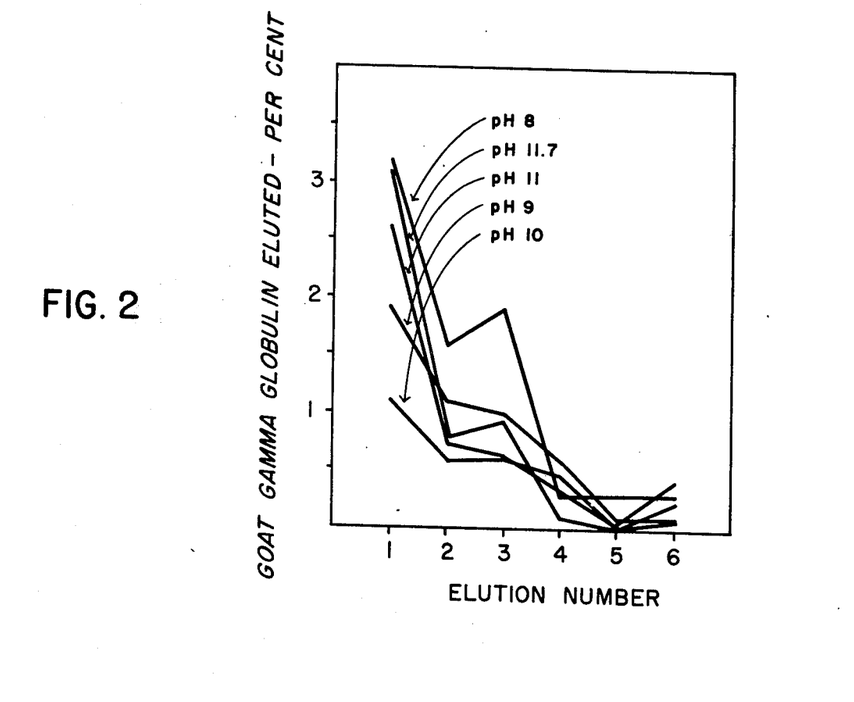
FIG. 2 shows the stability of immunoabsorbents prepared from agarose activated at various pHs. The mean (of three experiments) percent of the total bound GGG eluted in each of six successive 6 M urea sham elutions is shown for each pH of activation.

In FIG. 2 data on the stability of the immunoabsorbents prepared under standard conditions from agarose activated at varying pHs in the same three experiments are presented. The percent of GGG eluted as a fraction of the total GGG bound to the agarose is related to the pH of agarose activation. The percent figures represent means of data from three systematic experiments. The loss of GGG from these columns was small in all cases, and became very small or negligible after three sham elutions. Activation at pH 10.0 provided the most stable absorbent.

Because control of pH by adjustment with sodium hydroxide in an unbuffered system was difficult, an attempt was made to use 1.0 M sodium carbonate for adjusting the pH during cyanogen bromide activation. Much easier control of the pH was realized. However, in four successive experiments only from 1.2 to 10.6 percent of the GGG was coupled to agarose thus activated.

Successful activation of agarose was observed to be associated with a change in the physical character of the agarose gel to a more granular state. When this did not occur, little coupling of GGG was achieved.

EXAMPLE III

Figure 3:
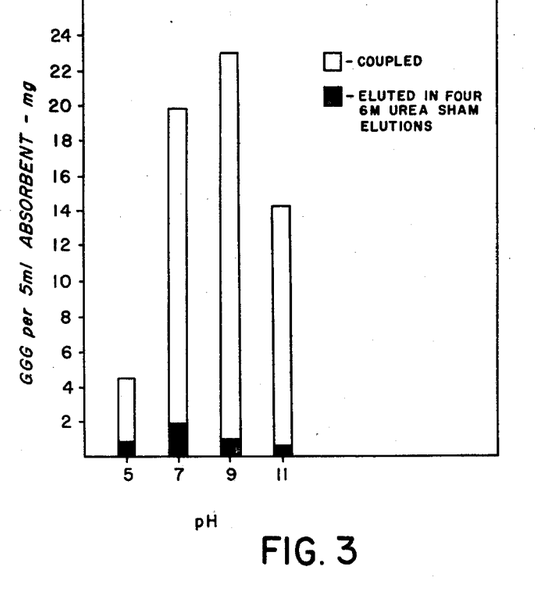
FIG. 3 shows the coupling of GGG to cyanogen bromide activated agarose at various pHs. The amount of GGG coupled to agarose is depicted for each of four pHs of coupling. The solid area of each bar represents the amount of GGG subsequently eluted in four sham elutions with 6 M urea.

The effect of pH and incubation time of the coupling reaction. The effect of pH and incubation time was studied in three experiments. The results are presented in Table 1. The data demonstrated that coupling is greater at pH 9.0 than at the other pHs tested. They also showed that an overnight incubation (16 hours) produced maximum coupling. Data on the stability of the immunoabsorbent during subsequent sham elutions with 6 M urea in relation to pH of coupling are presented in FIG. 3. It is clear that subsequent loss of GGG from the absorbent was small and that highly coupled absorbents were stable to urea.

The effect of GGG concentration on the coupling reaction. The amount of GGG bound to the agarose was found to be a function of the concentration of available GGG. Data from two representative experiments are presented in Table 2. At all concentrations of GGG tested, essentially all of the available GGG was bound to agarose activated at pH 10.0. Data on the stability of agarose-GGG absorbents in columns are also presented in Table 2. From 1.9 to 3.9 percent of the bound GGG was eluted in six urea elutions. The actual amount of GGG eluted in this fashion was as high as 4.1 mg and was directly related to the amount of GGG used for sensitization and bound to the agarose.

Data on the amount of culture filtrate antigen which could be bound to and subsequently eluted from immunoabsorbents prepared with different amounts of GGG are also presented in Table 2. The yield of CF antigen recovered from columns prepared with 5.1 mg GGG/ml of agarose was greater than that from columns prepared with 2.0 mg GGG/ml but did not increase further with higher concentrations of GGG.

Figure 4:
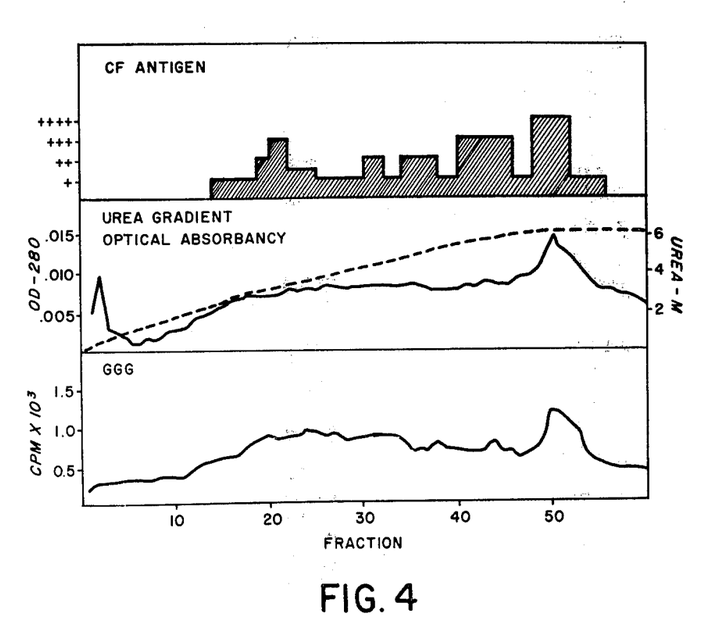
FIG. 4 depicts the urea gradient elution of culture filtrate antigen from immunoabsorbent column. In the center panel the urea gradient from 0 to 6 M is shown by the broken line and the elution chromatogram as monitored by optical absorbancy is shown by the solid line. In the upper panel the elution of culture filtrate antigen as estimated from the intensity of precipitin lines demonstrated by immunodiffusion is presented. In the lower panel the elution of GGG as detected by radioactivity is shown.

The effect of urea concentration elution. In an attempt to determine optimal concentrations of urea for elution, experiments were performed using an immunoabsorbent column eluted with a continuous gradient from 0 to 6.0 M urea in saline. The eluted fractions were monitored by optical absorbancy at 280 mu. GGG content of fractions was measured by radioactivity, and culture filtrate antigen was estimated semiquantitatively by immunodiffusion. As seen in FIG. 4 antigen elution began at approximately 3 M. Additional antigen was eluted through the subsequently increasing concentrations of urea, without an apparently optimal molarity. Goat gamma globulin was leached from the immunoabsorbent in a similar fashion, and it did not appear possible to achieve conditions which would preferentially elute culture filtrate antigen.

The recovery of absorbed culture filtrate antigen from immunoabsorbents was then studied using urea at increments of 0.5 molar from 4.0 to 6.0. For this purpose single batches of absorbent were divided into five identical columns and isotopically labelled culture filtrate was applied to each. In two such experiments no significant difference was observed in the antigen recovery using urea over the range of 4.0 to 6.0 molar. The data from one of these experiments are presented in Table 3. From the above experiment, it was concluded that elution should take place best at 3.0–6.0 molar.

EXAMPLE IV

The effect of urea upon culture filtrate antigens. In three separate experiments the effect of urea upon mycobacterial antigens has been studied by incubating culture filtrate in urea for 24 hours in concentrations of 6, 4, 2, 1, and 0 molar. At the end of incubation urea was removed by dialysis, the culture filtrate was lyophilized and reconstituted to a concentration of 10 mg dry weight/ml, and the antigenicity was assessed by skin testing sensitized guinea pigs and by immunoelectrophoresis. Dose response curves were obtained in the guinea pigs over the dose range of 0.4 to 10 mcg. The data are presented in Table 4. Concentrations of urea up to and including 4 M had no discernible effects on culture filtrate antigens. At 6 M urea, immunoelectrophoresis demonstrated a decrease in the amount of all recognizable antigens without qualitative changes in the immunoelectrophoretic pattern. Even at 6 M, skin test reactivity was not significantly affected.

Reuse of immunoabsorbents. In repeated experiments immunoabsorbent columns have been resued to purify antigen from additional aliquots of culture filtrate. Both product yield and contamination with GGG due to absorbent instability have been monitored. It has been 
found consistently that immunoabsorbents can be used four times without change in binding capacity or stability. However, this is only true when these columns are reused promptly, and simply allowing absorbents to sit for more than 24 hours has been found to lead to significant GGG contamination of eluted antigen.

EXAMPLE V

Product yield and antigenicity. Purified antigen recovered from immunoabsorbent columns which had been originally charged with $^{125}$I-labelled culture filtrate was pooled from several experiments and added as a tracer substance to whole culture filtrate. Five ml of this whole culture filtrate was counted and then used to prepare more antigen by chromatography on a column containing 5.0 ml of immunoabsorbent which was eluted with 6 M urea. Each fraction (5.0 ml) eluted was counted. Sensitized guinea pigs were skin tested with each fraction. Finally, the eluted antigen was pooled, subjected to immunoelectrophoresis, lyophilized to dryness, weighed in a tared vial, and recounted. In this way it was possible to calculate the product yield and to relate skin test reactivity to antigen dose. As seen in Table 5 approximately one-fifth of the antigen in the culture filtrate was recovered in this experiment. An additional three-fifths was recovered in the unabsorbed drop-through, wash fractions; this antigen has been recovered by rechromatography.

Figure 5:
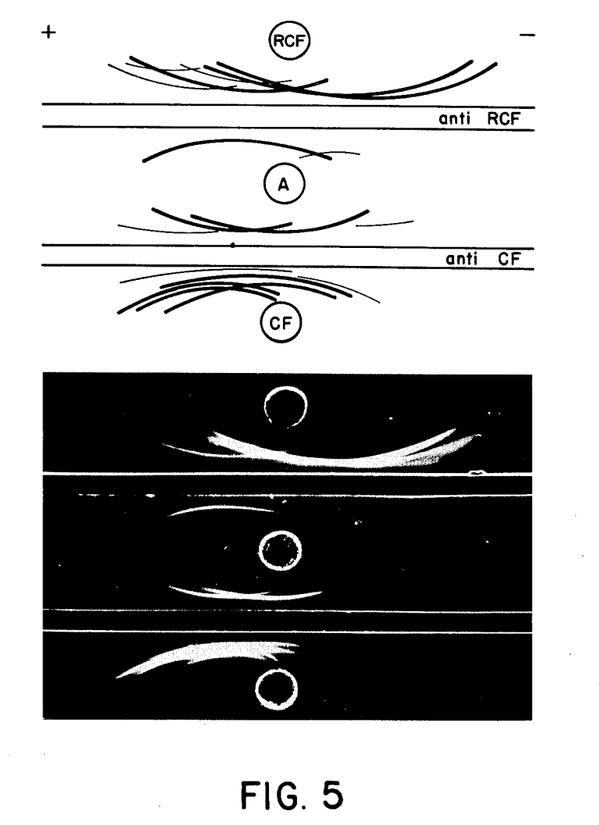
FIG. 5 shows immunoelectrophoresis of culture filtrate antigen recovered by urea elution from immunoabsorbent affinity chromatography column. The upper antigen well contained reference culture filtrate (RCF) antigen; the lower well contained the culture filtrate (CF) used in the present studies; the center well contained antigen (A) recovered by urea elution from specific immunoabsorbent columns. The upper antiserum trough contained reference anti-culture filtrate (anti RCF) antiserum; the lower trough contained the antiserum (anti CF) used to prepare immunoabsorbents in this study.

Immunoelectrophoresis, shown in FIG. 5, revealed that the recovered purified antigen product gave strong precipitin lines with antiserum. Skin test reactions in sensitized guinea pigs to successive fractions eluted with 6 M urea are shown in Table 6. The calculated antigen dose for each fraction is also shown. Both immediate and delayed reactions were observed in these animals, probably representing both Arthus and classic tuberculin reactions. When plotted semilogarithmically, the 24-hour delayed reactions gave the expected linear dose response curve.

EXAMPLE VI

Other mycobacteria. Affinity chromatography using immunoabsorbents has been found to be equally applicable to the purification of mycobacteria other than *M. tuberculosis*. It can be used to prepare antigens with species specificity for all of the other species of mycobacteria. For example, *Mycobacterium szulgai* was grown on synthetic medium to produce a culture filtrate and goat antiserum was prepared to *M. szulgai.* An immunoabsorbent was prepared from this antiserum by coupling to agarose beads with cyanogen bromide and this absorbent was used to purify *M. szulgai* antigen in a form suitable for the study of hypersensitivity to this organism. Antigens thus purified from other mycobacteria have improved specificity for the species from which they are prepared.

EXAMPLE VII

Culture filtrates of *Histoplasma capsulatum* were prepared in a manner similar to those described in Example 1. The procedural steps followed were identical with those earlier reported, in that the organism was grown on a synthetic medium to prepare a culture filtrate and a host animal was immunized and serum collected. This antiserum was then coupled to an activated substrate (agarose beads) to form an immunoabsorbent to which histoplasmin antigen was absorbed. The antigen was then eluted with 3–6 M urea at 7–11 pH (preferably 7–9 pH) to break the antigen-antibody bond and purified. In this fashion an improved antigen was prepared using affinity chromatography that helped in the study of hypersensitivity to histoplasmin.

EXAMPLE VIII

Next, culture filtrates of *Coccidioides imitus* were prepared, and the steps of the standard procedure repeated as in the examples above. Substantially similar results were obtained which helped in the study of hypersensitivity to coccidioidin.

EXAMPLE IX

The above procedure was then repeated in an experiment for *Blastomyces dermatitidis,* which is a dimorphic fungus, and in a separate experiment with saline extract of house dust, which is an example of an inhalant allergen. Both results proved satisfactory in developing a method of preparing antigens which is useful in the study of hypersensitivity and where antigenic specificity is important.

EXAMPLE X

In an effort to determine the range of substrates as a result of the principal work in the above experiments, another series of experiments were conducted using other substrates, such as cellulose, dextran and polyacrylamide, with standard materials.

When activated with cyanogen bromide in a manner similar to the standard conditions, cellulose and dextran beads performed adequately as substrates. Polyacrylamide gel beads were activated by the method of Inman and Dintzis [Inman, J. K., and Dintzis, H. M., 1969; Biochemistry 8:4074]. The most useful absorbents were obtained with agarose beads.

DISCUSSION OF EXAMPLES

Scores of investigators have attempted to fractionate crude tuberculin products to obtain isolated individual mycobacterial antigens. Well purified mycobacterial polysaccharides have been obtained by chemical extraction procedures previously known in this field. Protein antigens have been sought chiefly by physicochemical methods dependent upon molecular solubility, charge, or size. Only a few investigators have succeeded in isolating antigenic proteins in sufficient quanties to allow their subsequent study and characterization. In those cases multiple chromatographic procedures have been employed serially, and final product yields have been low.

The general method of affinity chromatography has been widely used in preparative biochemistry. With respect to mycobacterial antigens, this approach has been used by the inventor herein to isolate mycobacterial polysaccharides on the basis of their reactivity with concanavalin A. Immunoabsorbent affinity chromatography using specific antibody ligands on an inert substrate has had a much more limited application and has not been previously applied to the isolation of mycobacterial antigens. Most investigators using this method for the purification of antigens have eluted under conditions of very low pH, a condition which was avoided due to previous demonstration of acid lability of one of the major mycobacterial protein antigens. Chaotropic ions such as iodide or thiocyanate have been used for the elution of antigen from immunoabsorbents, but were found to be ineffective. Urea has had limited previous use as an eluting agent.

Despite the demonstrated general utility of immunoabsorbent affinity chromatography, little attempt has been made to study in a systematic fashion the optimal conditions for the preparation of absorbents with specific antibody globulin. In the present studies cyanogen bromide activation at pH 10.0 clearly gave maximal and most reproducible subsequent coupling of GGG to the agarose. Earlier studies using the coupling of glycine-leucine dipeptide to dextran gels (Sephadex) and their derivatives and to cellulose demonstrated maximum coupling after pH 11.5 cyanogen bromide activation. In the present study it was observed that GGG coupling to activated agarose is maximal at pH 9.0 and requires several hours of incubation, which is consistent with other data presented indicating that the optimal pH for this reaction is dependent upon the isoelectric point of the ligand.

Urea as an eluting agent has been used in concentrations of 8 M urea for antigen recovery and in concentrations of 6 M urea to elute reaginic antibody from a ragweed antigen absorbent. None of the prior investigators, however, attempted to use lesser concentrations of urea. The present data demonstrate that urea concentrations in the range of 3 – 6 M are preferred. Others found that guanidine would dissociate the hemoglobin-haptoglobin bond in an affinity chromatography system but only examined a variety of low concentrations of guanidine and concluded that 3.5 M was maximally effective provided that pH 5.0 was used.

The effect of the eluting agent upon the antigen being purified is clearly of importance. Urea concentrations above 4 M probably produced loss of antigenicity of mycobacterial proteins and other proteins but these antigens tolerated exposure to 4 M urea. Little attention has been given to the effect of eluants upon immunoabsorbents, and subsequent product contamination with dissociated ligand has not generally been considered by investigators using this approach. The use of radioactively labeled GGG permitted the measuring of this directly. Only small amounts of GGG were leached from the absorbent by urea and this could be minimized by the use of three preliminary sham elutions.

The utility of immunoabsorbent affinity chromatography for the purification of mycobacterial antigens ultimately depends upon the availability of monospecific antisera from which to prepare the immunoabsorbents. Since immunization with Freund's adjuvants usually leads to the production of antibody to many mycobacterial components, such monospecific antisera are not commonly available. The present method is capable of producing mycobacterial and other antigens of greater purity than any previously described single technique.

While there have been described herein what at present are considered to be the preferred embodiments of the instant invention, it will be readily appreciated by those skilled in the art that various changes and modifications may be made in the practice of the instant invention without departing from its spirit and scope.

TABLE 1

PER CENT OF AVAILABLE GGG COUPLED TO AGAROSE IN RELATION TO TIME AND pH

| pH | Coupling Time - Hours | | | | | | |
|----|---|---|---|---|---|---|---|
|  | 1 | 2 | 4 | 16 | 21 | 24 | 48 |
| 5 | 3.0 | 8.3 | 10.6 | | | 15.0 | |
| 7 | 12.6 | 18.7 | 21.7 | | | 35.3 | |
| 9 | 26.8 | 28.9 | 37.7 | | | 62.0 | |
| 11 | 19.2 | 22.6 | 28.0 | | | 46.2 | |
| 5 | 4.2 | 4.7 | | 10.6 | | 12.0 | 15.5 |
| 7 | 11.1 | 15.3 | | 36.4 | | 37.5 | 43.5 |
| 9 | 22.8 | 33.5 | | 61.3 | | 62.6 | 61.2 |
| 11 | 11.2 | 16.0 | | 37.8 | | 44.5 | 47.2 |
| 5 | | | | | 9.9 | | |
| 7 | | | | | 38.6 | | |
| 9 | | | | | 54.0 | | |
| 11 | | | | | 35.2 | | |

TABLE 2

EFFECT OF VARYING PROTEIN CONCENTRATION ON COUPLING OF GGG TO ACTIVATED AGAROSE AND SUBSEQUENT ABSORBENT STABILITY AND ANTIGEN RECOVERY. AGAROSE ACTIVATED AT pH 10.0

| Available GGG | GGG Coupled | | | Absorbent Stability GGG Eluted in Six 6 M Urea Elutions | | | CF Antigen Recovery | |
|---|---|---|---|---|---|---|---|---|
| mg/ml of agarose | CPM $\times 10^5$ | mg/ml of agarose | % of available GGG | CPM | total mg | % bound GGG | CPM $\times 10^5$ | % of total CF Radioactivity |
| 2.0 | .19 | 1.9 | 97.7 | 572 | .3 | 3.0 | .23 | 4.9 |
| 5.1 | .52 | 5.5 | 107 | 1160 | .6 | 2.4 | .47 | 9.8 |
| 10.2 | 1.00 | 10.5 | 103 | 1840 | 1.0 | 1.9 | .46 | 9.6 |
| 20.4 | 2.15 | 22.4 | 110 | 4460 | 2.4 | 2.2 | .43 | 8.9 |
| 2.0 | .19 | 2.0 | 102 | 292 | .2 | 1.6 | .32 | 6.0 |
| 5.1 | .55 | 5.8 | 112 | 1179 | .7 | 1.2 | .42 | 8.0 |
| 10.2 | 1.09 | 11.5 | 115 | 3324 | 1.8 | 3.1 | .41 | 7.8 |
| 20.4 | 1.95 | 20.6 | 103 | 7470 | 4.1 | 3.9 | .50 | 9.5 |

TABLE 3

RECOVERY OF ABSORBED CULTURE FILTRATE ANTIGEN AS A FUNCTION OF CONCENTRATION OF UREA USED FOR ELUTION

| Urea Molarity | Total CF Antigen Applied (CPM $\times 10^4$) | CF Antigen Recovered (CPM $\times 10^4$) | Antigen Recovery (% of Total CPM) |
|---|---|---|---|
| 4.0 | 39.3 | 7.15 | 18% |
| 4.5 | 38.0 | 5.03 | 13% |
| 5.0 | 38.5 | 5.26 | 14% |
| 5.5 | 44.9 | 7.48 | 17% |
| 6.0 | 38.1 | 6.13 | 16% |

TABLE 4

SKIN TEST REACTIONS IN SENSITIZED GUINEA PIGS TO CULTURE FILTRATE INCUBATED WITH UREA

| Urea Concentration | Antigen Dose (mcg) | Mean Reaction Diameter (mm) ± Standard Error | | |
|---|---|---|---|---|
|  |  | 4 hrs | 24 hrs. | 48 hrs |
| 6 M | 10.0 | 12.0±0.9 | 12.4±1.3 | 6.4±0.7 |
|  | 2.0 | 8.8±1.6 | 9.2±1.2 | 2.8±0.9 |
|  | 0.4 | 7.4±1.3 | 6.6±0.7 | 0 |
| 4 M | 10.0 | 12.8±0.4 | 13.0±0.5 | 8.8±0.6 |
|  | 2.0 | 11.2±0.4 | 11.0±0.4 | 5.4±0.7 |
|  | 0.4 | 8.6±0.8 | 7.6±0.4 | 1.5±0.5 |
| 2M | 10.0 | 13.6±0.9 | 13.6±0.7 | 9.8±1.3 |
|  | 2.0 | 12.0±0.5 | 10.2±0.8 | 5.8±1.5 |
|  | 0.4 | 9.4±0.9 | 7.8±0.7 | 1.4±0.9 |
| None | 10.0 | 11.0±1.0 | 12.8±1.0 | 8.2±0.8 |
|  | 2.0 | 7.0±0.8 | 8.6±1.2 | 3.8±1.0 |
|  | 0.4 | 5.6±1.8 | 7.6±0.9 | 0 |

TABLE 4-continued

| SKIN TEST REACTIONS IN SENSITIZED GUINEA PIGS TO CULTURE FILTRATE INCUBATED WITH UREA | | | | |
|---|---|---|---|---|
| Urea | Antigen Dose | Mean Reaction Diameter (mm) ± Standard Error | | |
| Concentration | (mcg) | 4 hrs | 24 hrs. | 48 hrs |
| Urea Control | | 2.0±1.2 | 0 | 0 |

TABLE 5

| ANTIGEN YIELD FROM IMMUNOABSORBENT CHROMATOGRAPHY | | | |
|---|---|---|---|
| | CPM | mcg | % |
| Total Applied to Column | 7152 | 273.2 | |
| Recovered in Wash (not absorbed) | 4169 | 159.3 | 58.3 |
| Eluted with Urea After Absorption | 1550 | 59.2 | 21.7 |
| Present in Inter-Peak Zone | 380 | 14.5 | 5.3 |
| Lost (not recovered) | 1043 | 39.8 | 14.6 |

TABLE 6

| SKIN TEST REACTIONS IN SENSITIZED GUINEA PIGS TO SUCCESSIVE FRACTIONS ELUTED FROM IMMUNOABSORBENT WITH 6 M UREA | | | | |
|---|---|---|---|---|
| Fraction | Antigen Dose | Mean Reaction Diameter (mm) ± Standard Error | | |
| Number | (mcg) | 4 hrs | 24 hrs | 48 hrs |
| 1 | 0.50 | 11.2±0.9 | 12.2±1.4 | 6.6±0.5 |
| 2 | 0.34 | 10.0±0.6 | 11.8±0.7 | 6.6±1.0 |
| 3 | 0.15 | 8.4±0.8 | 9.8±0.7 | 7.0±0.6 |
| 4 | 0.13 | 7.6±0.5 | 9.2±0.9 | 6.2±0.7 |
| 5 | 0.05 | 6.0±0.6 | 7.8±0.7 | 5.2±0.7 |
| 6 | 0.06 | 5.0±0.8 | 7.2±1.0 | 3.8±0.5 |
| 7 | 0.02 | 4.6±0.5 | 6.4±0.5 | 2.0±0.8 |
| Urea Control | | 0 | 0 | 0 |
| PBS Control | | 0.6±0.5 | 0 | 0 |

What is claimed is:

1. A process for the preparation of an antigen for the recognition and measurement of hypersensitivity where antigenic specificity is desired by immunoabsorbent affinity chromatography, comprising:

- coupling antibodies to an appropriate inert substrate by chemical bonding to form an absorbent in which said specific antibody acts as a ligand;
- preparing crude mixtures containing desired said antigen;
- absorbing said antigen from said crude mixtures containing said antigen by the said prepared absorbent;
- eluting the desired said antigen from said absorbent using 3–6 molar urea at PN 7 - 9
- recovering the purified antigen.

2. The process as recited in claim 1 wherein said hypersensitivity is to tuberculin.

3. The process as recited in claim 1 wherein said hypersensitivity is derived from species of Mycobacteria other than *M. tuberculosis.*

4. The process as recited in claim 1 wherein said hypersensitivity is to histoplasmin.

5. The process as recited in claim 1 wherein said hypersensitivity is to coccidioidin.

6. The process as recited in claim 1 wherein said hypersensitivity is to blastomycin.

7. The process as recited in claim wherein said appropriate inert substrate is agarose beads.

8. The process as recited in claim 1 wherein said appropriate inert substrate is cellulose.

9. The process as recited in claim 1 wherein said appropriate inert substrate is dextran beads.

10. The process as recited in claim 1 wherein said appropriate inert substrate is polyacrylamide gel beads.

11. The process as recited in claim 1 wherein said chemical bond is formed through a reaction with cyanogen bromide.

12. The process as recited in claim 1 wherein said crude mixture is a bacterial culture filtrate.

13. The process as recited in claim 1 wherein said crude mixture is a bacterial cell extract.

14. The process as recited in claim 1 wherein said crude mixture is a fungal culture filtrate.

15. The process as recited in claim 1 wherein said crude mixture is a fungal cell extract.

16. The process as recited in claim 1 wherein said condition which breaks the antigen-antibody bond is 4 Molar urea at pH 9.

17. A process for the preparation of diagnostic skin testing reagents by immunoabsorbent affinity chromatography suitable for use in tuberculin skin testing and in vitro study of cell-mediated tuberculin hypersensitivity, comprising:

- immunizing a suitable host animal with an antigen derived from mycobacteria;
- collecting antisera from said immunized animal and selecting the most highly specific of said antisera;
- isolating the antibody-containing gamma globulin from said selected antisera;
- coupling said antibody-containing gamma globulin to an appropriate inert substrate by chemical bonding to form an absorbent in which the specific antibody acts as a ligand;
- preparing crude mycobacterial culture filtrates containing desired said antigen;
- absorbing said antigen from said crude mycobacterial culture filtrates by said prepared absorbent;
- eluting the desired antigen from said absorbent using 3 - 6 Molar urea at pH 7 - 9;
- recovering the purified antigen and further purifying said antigen to remove trace contaminants of said gamma globulin or mycobacterial polysaccharides by physicochemical methods; and
- preparing said antigen in appropriate sterile form suitable for clinical use.

18. The process as recited in claim 17 wherein said mycobacterium is *Mycobacterium tuberculosis.*

19. The process as recited in claim 17 wherein said mycobacterium is a species other than *M. tuberculosis.*

20. The process as recited in claim 17 wherein said appropriate inert substrate is agarose beads.

21. The process as recited in claim 17 wherein said appropriate inert substrate is cellulose.

22. The process as recited in claim 17 wherein said chemical bond is formed by the reaction with cyanogen bromide.

23. The process as recited in claim 17 wherein said eluting is accomplished by using 4 Molar urea at pH 9.

24. A process for the preparation of improved tuberculin skin testing reagents suitable for use in diagnostic tuberculin skin testing by immunoabsorbent affinity chromatography, comprising:

- immunizing a goat with an antigen derived from culture filtrates of *Mycobacterium tuberculosis;*
- collecting antisera from said immunized animal and selecting the most highly specific of the available said antisera;
- isolating the antibody-containing gamma globulin from the selected said antisera;
- chemically coupling said antibody-containing gamma globulin to agarose beads by reaction with cyanogen bromide to form an immunoabsorbent in which the specific said antibody acts as a ligand;

preparing crude, unheated, mycobacterial culture filtrate containing said antigen;

absorbing the desired said antigen from said crude, unheated mycobacterial culture filtrate with said prepared absorbent;

eluting said desired antigen from said absorbent using 4 Molar urea buffered to pH 9.0 with sodium bicarbonate; and recovering the purified said desired antigen.

25. An improved tuberculin antigen derived from unheated culture filtrate of *Mycobacterium tuberculosis* as prepared by the process recited in claim 24 and characterized by its high purity, high activity and improved species specificity; said prepared antigen further being characterized as a glycoprotein which stains with Coomasie Blue protein stain but does not stain with periodic acid-Schiff and Alcian Blue stains for polysaccharides; the said prepared antigen further being characterized in that it combines with concanavalin A and contains a carbohydrate moiety probably containing mannose, and in 7.0 percent acrylamide gel with electrophoresis at pH 9.5 has an Rf of 0.61, and is identified immunologically as antigen 5.

26. An improved tuberculin antigen derived from unheated culture filtrate of *Mycobacterium tuberculosis* as prepared by the process recited in claim 24 and characterized by its high purity and high activity and containing both specific and nonspecific antigenic determinant sites; said prepared antigen may be hydrolyzed into tuberculin active peptides by treatment with hydrochloric acid and characterized as a protein with a molecular weight estimated by gel filtration of 45,000–48,000 daltons and having a sedimentation constant of 2.8 svedbergs, and in 7.0 percent acrylamide gel with electrophoresis at pH 9.5 has an Rf of 0.68, and is identified as antigen 6.

* * * * *